United States Patent
Hue et al.

(10) Patent No.: US 10,843,536 B2
(45) Date of Patent: Nov. 24, 2020

(54) SECTORIZED ADAPTIVE SCREEN AND DRIVER ASSISTANCE SYSTEM COMPRISING SUCH AN ADAPTIVE SCREEN

(71) Applicant: VALEO VISION, Bobigny (FR)

(72) Inventors: David Hue, Bobigny (FR); Kedar Sathaye, Bobigny (FR); Jean-Louis De Bougrenet, Bobigny (FR); Emmanuel Daniel, Bobigny (FR); Laurent Dupont, Bobigny (FR); Samir Abbas, Bobigny (FR); Samir Bentahar, Bobigny (FR)

(73) Assignee: VALEO VISION, Bobigny (FR)

( * ) Notice: Subject to any disclaimer, the term of this patent is extended or adjusted under 35 U.S.C. 154(b) by 0 days.

(21) Appl. No.: 15/873,467

(22) Filed: Jan. 17, 2018

(65) Prior Publication Data

US 2018/0201101 A1    Jul. 19, 2018

(30) Foreign Application Priority Data

Jan. 17, 2017 (FR) ..................... 17 50332

(51) Int. Cl.
*B60J 3/04* (2006.01)
*G02F 1/133* (2006.01)
(Continued)

(52) U.S. Cl.
CPC .............. *B60J 3/04* (2013.01); *A61F 9/023* (2013.01); *B60J 3/06* (2013.01); *G02C 7/101* (2013.01);
(Continued)

(58) Field of Classification Search
CPC ..... B60J 3/04; B60J 3/06; A61F 9/023; G02F 1/13306; G02F 1/13318; G02F 1/134309; G02F 1/13725; G02C 7/16; G02C 7/101
(Continued)

(56) References Cited

U.S. PATENT DOCUMENTS

2011/0292041 A1* 12/2011 Lee ................ G09G 3/342
                                                        345/419
2013/0215376 A1*  8/2013 Guo ................ G02C 7/101
                                                        351/159.39
(Continued)

FOREIGN PATENT DOCUMENTS

FR      2 693 562        1/1994
FR      3 010 941        3/2015
WO   WO 03/005942 A1     1/2003

OTHER PUBLICATIONS

French Preliminary Search Report dated Sep. 14, 2017 in French Application 17 50332 filed on Jan. 17, 2017 (with English Translation of Categories of Cited Documents).

*Primary Examiner* — Nathanael R Briggs
*Assistant Examiner* — William D Peterson
(74) *Attorney, Agent, or Firm* — Oblon, McClelland, Maier & Neustadt, L.L.P.

(57) ABSTRACT

An adaptive screen including at least one liquid crystal shutter. At least one of the shutters includes at least two active zones which are addressed by a control signal which permits the switchover of the at least one corresponding shutter between a passing configuration, in which a transmittance is equal to a maximum value, and a blocking configuration, in which the transmittance is equal to a minimum value. A "principal" active zone covers a surface area of the adaptive screen which is equal to or lower than 60% of the surface area of the adaptive screen, in order to reduce the response time of the principal active zone.

18 Claims, 2 Drawing Sheets

(51) Int. Cl.
    *G02C 7/16*     (2006.01)
    *A61F 9/02*     (2006.01)
    *B60J 3/06*     (2006.01)
    *G02C 7/10*     (2006.01)
    *G02F 1/1343*     (2006.01)
    *G02F 1/137*     (2006.01)

(52) U.S. Cl.
    CPC ........... *G02C 7/16* (2013.01); *G02F 1/13318* (2013.01); *G02F 1/134309* (2013.01); *G02F 1/13306* (2013.01); *G02F 1/13725* (2013.01)

(58) Field of Classification Search
    USPC .......................................................... 349/16
    See application file for complete search history.

(56) References Cited

U.S. PATENT DOCUMENTS

| | | | |
|---|---|---|---|
| 2014/0226096 A1* | 8/2014 | Taheri | G02F 1/13306 349/33 |
| 2016/0214467 A1 | 7/2016 | El Idrissi et al. | |

\* cited by examiner

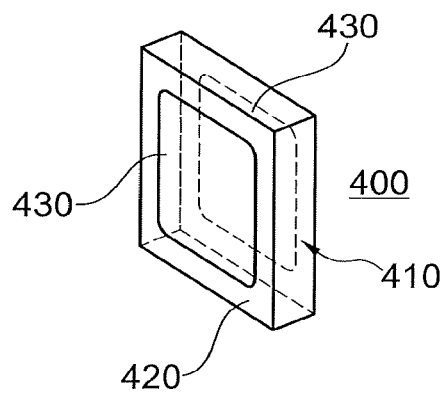
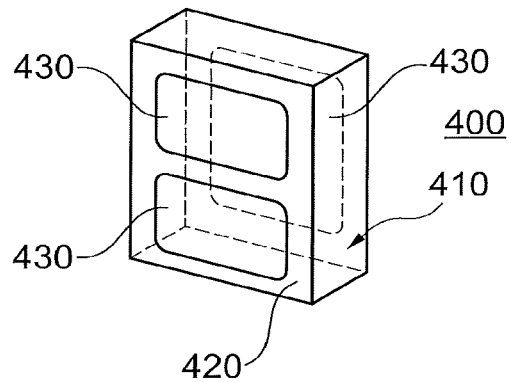
Fig. 1a      Fig. 1b
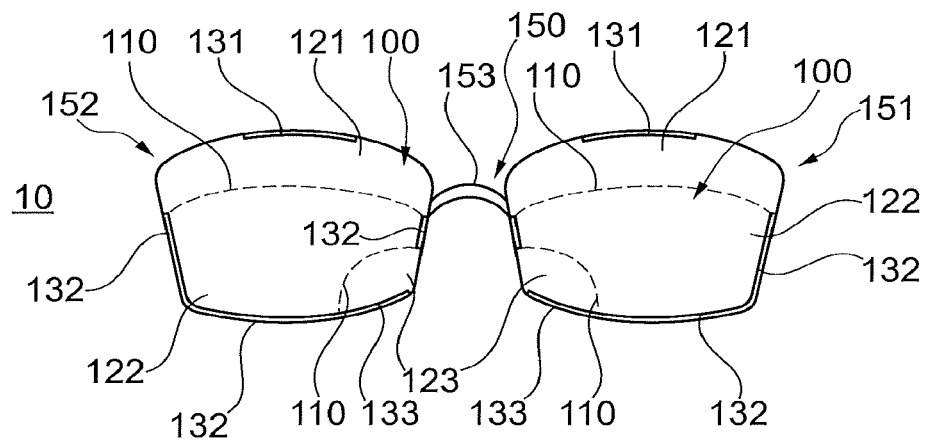
Fig. 2a
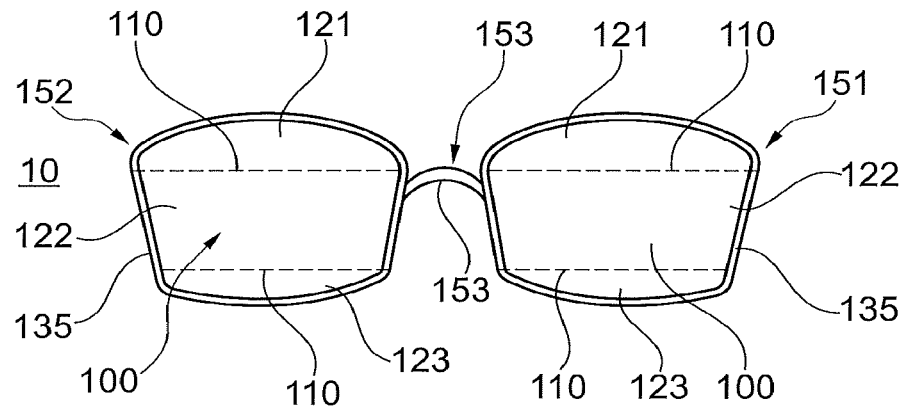
Fig. 2b

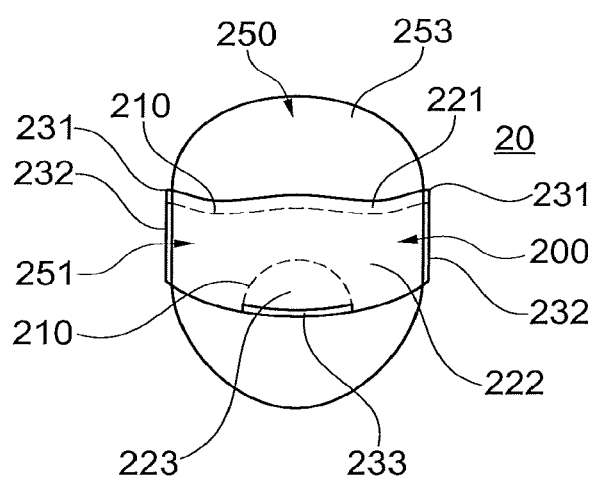
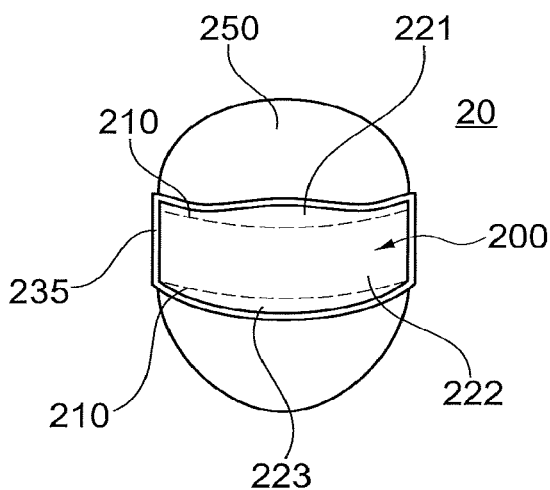
Fig. 3a    Fig. 3b
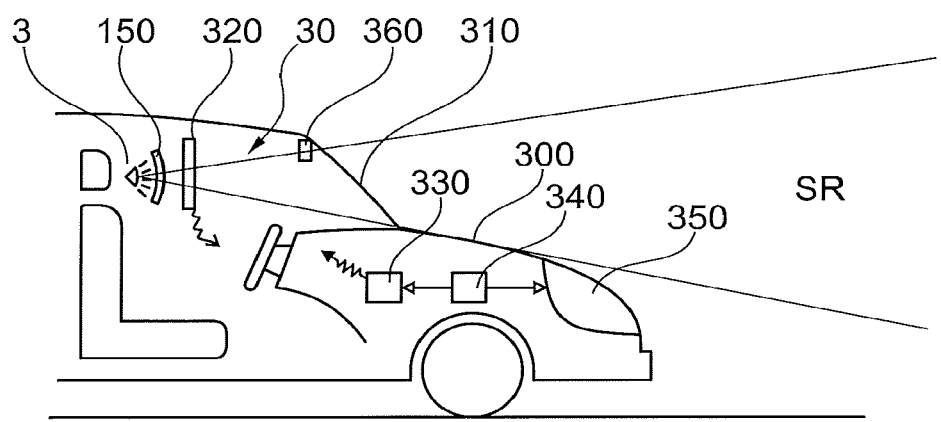
Fig. 4

SECTORIZED ADAPTIVE SCREEN AND DRIVER ASSISTANCE SYSTEM COMPRISING SUCH AN ADAPTIVE SCREEN

TECHNICAL FIELD

The present invention relates to an adaptive screen. It is included in the field of anti-glare protection devices, and more specifically in the context of motor vehicles. The present invention further relates to a driver assistance system comprising such an adaptive screen.

PRIOR ART

Static glasses are known, specifically for use in sunglasses, which permit the reduction of glare experienced by the wearer of said sunglasses. Static glasses can be, for example, of the simple coloured glass type, of uniform colour or with graduated coloration. These glasses are described as static, as they do not incorporate any dynamic elements which permit the adjustment of a coefficient of light transmission through said glasses as a function of ambient brightness: the colour shade of static glasses is fixed, and cannot be modified after the manufacture thereof. Only the optical density of glasses is predefined at the time of manufacture, in order to predefine, in a static and non-modifiable manlier, the transmission coefficient of said glasses. One disadvantage of static glasses is that it is not possible to modulate the luminous intensity transmitted by said glasses as a function of an incident luminous intensity and/or as a function of a certain threshold level of luminous intensity transmitted by the static glasses.

In response to this requirement for adaptability, the document FR 2 975 792 is also known, which discloses spectacles comprising dynamic glasses, which are formed by a layer of liquid crystals captured between two transparent lenses. The transmittance of liquid crystals is modulated as a function of the luminous intensity measured by a photodetector situated on the spectacles. One disadvantage of dynamic glasses is associated with the response time, which is relatively long as a function of the surface area of said dynamic glasses. As a result, the darkening of known active glasses is only achieved after a few tenths of a second, or even after several seconds, thereby rendering them unsuitable for certain situations, specifically in the context of driving a motor vehicle, for example. In practice, in the case of a journey in sunny weather, during which the driver enters a region of rapid and substantial luminous transition such as, for example, the entrance to a tunnel, the response time of known active glasses substantially exceeds the duration of luminous transition in said region. As a result, the driver of the motor vehicle is generally constrained to remove their spectacles, if they wish to continue to correctly perceive the view of the road on which they are then driving.

In a comparable manner, in the case of night-time driving, contrasts in luminous intensity in the view of the road—specifically in the event of the crossover of other vehicles or the entry of the vehicle into a lit zone—are such that it is essential to minimize the response time of active glasses, if the use thereof is not to be rendered completely inconvenient, if not impossible.

Finally, document FR 6 011 095 is known, which discloses an adaptive optical filter for spectacle glass comprising at least two separate zones which incorporate liquid crystals, such that its optical transmission state can be adjusted between an opaque state and a transparent state. The technical issue resolved by this document is to permit the transition from one optical transmission state to another in a progressive manner. However, this document does not endeavour to reduce the response time of spectacles as a function of a sudden variation in the luminous intensity perceived by the wearer of the spectacles. The spectacles disclosed in this document are not suitable for use during night-time driving.

The object of the present invention is the resolution of the above-mentioned problems, at least to a substantial degree, together with the provision of further advantages.

A further object of the invention is the proposal of a novel adaptive screen for the resolution of at least one of these problems.

A further object of the present invention is the reduction of the response time of at least part of such an adaptive screen.

A further object of the invention is the reduction of the electricity consumption of such an adaptive screen.

A further object of the invention is the improvement of the convenience of use of such an adaptive screen.

PRESENTATION OF THE INVENTION

According to a first aspect of the invention, at least one of the above-mentioned objectives is fulfilled by an adaptive screen comprising at least one liquid crystal shutter, wherein at least one of the shutters comprises at least two active zones which are addressed by a control signal which permits the switchover of the at least one corresponding shutter between a passing configuration, in which a transmittance is equal to a maximum value, and a blocking configuration, in which the transmittance is equal to a minimum value, characterized in that a "principal" active zone covers a surface area of the adaptive screen which is equal to or lower than 60% of the surface area of said adaptive screen, in order to reduce the response time of said principal active zone, and preferably ranges between 50% and 60% of the surface area of the adaptive screen.

The adaptive screen according to the first aspect of the invention thus permits the division of said adaptive screen into a plurality of active zones, the average transmittance of each of which can be controlled in an independent manner by means of the corresponding control signal: the shutter(s) in the corresponding active zone thus switch over between two transmittance states, in accordance with a specific operating regime.

The operating regime of the shutters is defined by the corresponding control signal, which controls the switchover thereof, more specifically by means of at least certain of its temporal characteristics, as described hereinafter.

The invention, according to its first aspect, thus permits the reduction of the surface areas of each active zone, in order to minimize the response time of at least the principal active zone. Thus, by the replacement of a single active zone which covers the entire surface area of the adaptive screen with the plurality of active zones, it is possible to achieve the more rapid modification of the transmittance of the adaptive screen and/or the transmittance of at least one of the active zones, as a function of a variation in the corresponding control signal.

Specifically, the electrical energy required to execute the switchover of the shutters in each active zone from one transmittance state to the other is simultaneously dependent upon the surface area of the active zones and upon the operating regime applied to said active zone. More specifically, the electrical energy required for the switchover of shutters is proportional to the surface area of an active zone considered, and to the operating regime to which the latter is subjected. The operating regime of shutters affects the response time of the corresponding active zone, specifically by means of a rate of repetition of transitions between the two transmittance states of the shutters. The rate of repetition is specifically dependent upon the frequency and/or the phase and/or the duty cycle of the control signal.

The principal active zone of the adaptive screen thus has a reduced surface area, in relation to that of an adaptive screen of an equivalent type from the prior art; additionally, the surface area of the principal active zone has a surface area which is smaller than that of the constituent adaptive screen thereof, such that the consumption of electrical energy required to achieve a change from one transmission state to the other, and/or to execute the switchover of the constituent shutters thereof, is reduced.

Each shutter is configured to switch over—according to an operating regime which is dependent upon the control signal—between the blocking configuration, in which its transmittance is equal to the minimum value, for example equal to 0 or close to 0, and the passing configuration, in which its transmittance is equal to the maximum value, for example equal to 1 or close to 1.

The average transmittance of the active zone is thus defined by the temporal average, considered over a given integration time, of the transmittances of each constituent shutter of said active zone. More specifically, the average transmittance is calculated over a duration corresponding to a number of switching cycles of the constituent shutters of said active zone, for example greater than several hundred cycles.

An instantaneous transmittance is also defined, wherein the temporal average of the transmittance of each constituent shutter of the active zone is calculated over a duration corresponding to a number of oscillation cycles of said shutters, for example between several tens and several hundreds of cycles. In other words, the instantaneous transmittance corresponds to the average transmittance, calculated over a shorter integration time.

The term average transmittance is understood here in its broadest sense, and specifically according to one of the two above-mentioned interpretations.

It is thus possible to control each shutter in the adaptive screen according to a different regime, in order to control the corresponding configuration of the active zone(s) formed by each shutter. By way of non-limiting example:

the average transmittance of a first active zone can be configured such that it is close to zero, wherein the active zone is completely, or virtually completely occulted, and/or the average transmittance of a second active zone can be configured such that it is close to 1, wherein the active zone is completely, or virtually completely transparent, and/or the average transmittance of a third active zone can be configured such that it is equal to an intermediate value, for example close to 0.5.

An average transmittance tending towards zero permits the attenuation of the luminous flux which traverses the corresponding active zone, thus permitting the prevention of glare or discomfort, where the luminous flux reaching the screen is very substantial. Conversely, an average transmittance tending towards 1 permits the passage of a luminous flux traversing the corresponding active zone with limited attenuation, or no attenuation whatsoever. Such an average transmittance value is particularly appropriate for conditions of low brightness in which, for example, the intensity of the luminous flux reaching the screen is sufficiently low to prevent the occurrence of any glare or discomfort.

According to other forms of embodiment, the number, surface area and shape of the active zones, together with the variety of operating regimes, may differ as a function of the applications and requirements desired. Specifically, certain active zones can be controlled by an identical control signal. In a highly specific manner, the present invention specifically proposes an active screen comprising a plurality of active zones, all of which are controlled by one and the same control signal, or by a plurality of identical control signals. Such an adaptive screen, although apparently comprising a single surface area of variable transmittance, nevertheless shows a shorter response time than known adaptive screens, as a result of the division thereof into a plurality of active zones.

The adaptive screen according to the first aspect of the invention can advantageously comprise at least one of the refinements described below, wherein the technical characteristics constituting said refinements can be considered individually or in combination:

the at least one shutter is accommodated between a first and/or a second transparent medium. The first and/or the second transparent medium can form a lens, such that the trajectory of at least one ray of light respectively traversing the first and/or the second transparent medium is modified. The lens or lenses thus formed can be used, for example, to correct a known ophthalmological disorder, such as myopia or astigmatism;

the adaptive screen comprises at least three electrodes, a first part of which is situated on a first side of the at least one shutter, and a second part of which is situated on a second side of the at least one shutter, wherein the electrodes permit the application of a non-zero electric field in respect of each other, for the configuration of the at least one shutter of each active zone in the passing or blocking configuration, wherein each active zone can be configured independently of the other active zones. In a more specific manner, an active zone formed by at least one liquid crystal shutter can comprise a first polarizing filter, described as a polarizer, and/or a second polarizing filter, described as an analyzer, and at least one liquid crystal layer situated between the polarizer and the analyzer. The electrodes are secured to the surfaces of the polarizing filters, in a position facing the liquid crystals. The application of the electric field between two opposing electrodes in relation to the corresponding shutter permits the electrical polarization of the liquid crystal layer according to a specific optical polarization state. Each electrical polarization state has a corresponding optical polarization state and, ultimately, a state of average transmittance in the corresponding active zone. Accordingly, the application of a variable—and, more specifically, periodic—electric field permits the modification of the optical polarization state of shutters in the corresponding active zone—more specifically, in a periodic manner—and thus the modification of the state of transmittance of the corresponding active zone. Each electrode is advantageously arranged on either side of the shutters, for example against each surface of the transparent media facing said shutters. Alternatively, the adaptive screen comprises at least three electrodes, a first part of which is situated on a first side of the at least one shutter, and a second part of which is situated on a second side of the at least one shutter, wherein the electrodes permit the application of a non-zero electric field in respect of each other, for the configuration of the at least one shutter of each active zone in the passing or blocking configuration, wherein each active zone can be configured independently of the other active zones. More specifically, an active zone formed by at least one shutter can comprise a dichroic and/or chiral dopant. The electrodes are secured to opposing surfaces, in a position facing the liquid crystals. The application of an electric field between two opposing electrodes in relation to the corresponding shutter permits the changeover of the molecules forming the dichroic and/or chiral dopant between a first state, in which they reflect a ray of incident light, and a second state, in which they absorb a ray of incident light. Ultimately, an average state of transmittance of the corresponding active zone can be achieved as a function of a duty cycle between the absorbent and reflective states of said dichroic colorant molecules. Each electrode is advantageously arranged on either side of the shutters, for example against each surface of the transparent media facing said shutters;

the adaptive screen comprises electrical conductors for the conduction of the control signal to at least one part of the electrodes. More specifically, one electrical conductor is electrically connected to the first electrode, a second electrical conductor is connected to the second electrode, and a third electrical conductor is connected to the third electrode;

the electrical conductors are electrically connected to each of the electrodes via at least one electrical connection interface, wherein each electrical connection interface extends over the length of an active zone;

the electrical connection interface extends peripherally to at least one active zone and, more specifically, at the level of at least one part of the inactive zones;

the electrical connection interface extends peripherally to the adaptive screen, such that it is not visible through said adaptive screen;

at least one electrical connection interface extends over the length of the corresponding active zone, to a distance ranging from 0.1 cm to 2.5 cm. Advantageously, each active zone comprises two electrical connection interfaces of length substantially equal to 4 mm, and spaced by at least one millimetre;

the at least one shutter is configured as a function of at least one parameter of the control signal, wherein the parameter is selected from a switching frequency and/or a switching phase and/or a switching duty cycle. Accordingly, the temporal parameters of the control signal permit the application of a variable electrical field to at least one part of the active zones and, more specifically, to the constituent shutters of said active zones. As described above, the application of such an electric field permits the modification of the optical polarization state—in the case where the shutter is associated with at least one polarizing filter—or of the optical absorption and/or reflection state—in the case where the shutter is associated with a dichroic and/or chiral dopant. The modification of these states permits the switchover of the shutter between various corresponding transmittance states, as defined above. Preferably, the control signal is periodic, thereby permitting the control of the transmittance state of the corresponding active zone;

the control signal is of the pulse width modulation type, described as a PWM control signal. More generally, the control signal is of the periodic electric signal type, preferably digital, the oscillation frequency of which ranges from 100 Hz to 1 kHz. The use of a periodic signal advantageously permits an increase in the rate of repetition of transitions between the two polarization and/or transmittance states of the at least one shutter, thereby minimizing the electrical energy required for the operation of the corresponding active zone and, more generally, of the adaptive screen. Naturally, according to the dimensions of the adaptive screen, the response time of the various active zones can vary. In general, however, the adaptive screen according to the first aspect of the invention permits the reduction of the response time of at least one active zone, in relation to an adaptive screen of identical size comprising only a single active zone;

the switching frequency of the at least one shutter of the principal active zone is equal to or greater than 200 Hz, such that switching operations of said at least one shutter of the principal active zone are rendered imperceptible to the human eye. Where applicable, the switching frequency of the at least one shutter of the principal active zone is greater than that of at least one other active zone of the adaptive screen. Thus, for a given level of electrical energy, this advantageous characteristic permits an increase in the rate of repetition in the principal active zone and, by way of a priority, the functional optimization of said principal zone in relation to other active zones of the adaptive screen, specifically by minimizing the response time thereof;

each active zone is delimited and/or separated from another active zone by an inactive zone. An active zone is defined as being a zone of the adaptive screen which incorporates no shutters or, alternatively, as being a zone in which the at least one shutter receives no electrical transmission, such that no electrical field can be applied to the terminals thereof, for the modification of the polarization and/or transmittance state thereof. Preferably, at least the active zones which are situated in the central zones of the adaptive screen are transparent. Preferably, the inactive zones comprise at least one part of the electrical connection interfaces;

the width of the inactive zone is less than 2 µm, such that the latter are rendered imperceptible to the human eye;

the active zones are arranged adjacently, two-by-two, wherein each active zone extends from one edge of the adaptive screen to the other. According to a first form of embodiment, the active zones are configured in horizontal strips, wherein the active zones are arranged adjacently, two-by-two, in the vertical direction, each active zone being separated from the adjacent active zone by an inactive zone. According to a second form of embodiment, the active zones are configured in vertical strips, wherein the active zones are arranged adjacently, two-by-two, in the horizontal direction, each active zone being separated from the adjacent active zone by an inactive zone. According to further forms of embodiment, the active zones can extend in any direction, according to the applications considered. Where applicable, active zones can constitute varying geometrical zones in order, for example, to match certain specific ophthalmological zones such as, for example, a first zone which is adapted to near sight, and a second zone which is adapted to long sight. Further configurations are described hereinafter, by way of examples.

According to a second aspect of the invention, an optical protection device is proposed, comprising an adaptive screen according to the first aspect of the invention, or according to any of the refinements thereof, and a support which is designed to maintain the adaptive screen in front of the eyes of an individual wearing said optical protection device, wherein the principal active zone of the adaptive screen is positioned in a central zone of the adaptive screen and extends laterally from one edge of the adaptive screen to the other, wherein the surface area of said driving zone is equal to or less than 60% of the surface area of the adaptive screen.

According to its second aspect, the invention thus permits the improvement of the visual comfort of the individual who wears the optical protection device, specifically with respect to the brightness perceived by said individual. More specifically, it is possible to configure each active zone of the adaptive screen of the optical protection device according to the second aspect of the invention as a function of the ambient brightness, and more specifically as a function of the brightness of a view perceived by the individual through said adaptive screen.

In a further and more specific manner, the invention, according to its second aspect, advantageously permits the configuration of the transmittance of each active zone as a function of the part of the view which is situated in the axis of each corresponding active zone, in relation to the eyes of the individual. The transmittance of each active zone is thus configured in order to obtain the compliance of a given luminance transmitted with a predefined luminance value.

For a given light source, luminance transmitted is defined by the luminance perceived by an individual from behind the adaptive screen, in comparison with an "incident" luminance, corresponding to the luminance of said light source.

For reference, in photometry, perceived luminance or visual luminance, commonly described as luminance, is defined as the quotient of luminous intensity of the source surface area by unit area of said source projected onto a perpendicular plane in the direction of observation. The SI unit of luminance is the candela per square metre ($cd \cdot m^{-2}$); it is also dependent upon the sensitivity of the human eye.

Such an optical protection device can be configured, for example, such that the luminance transmitted is uniform, or substantially uniform, over part of the surface area of the adaptive screen. In other words, the optical protection device can be configured such that an equal quantity of light rays pass through at least one part of the active zones per unit of time. At the very least, the optical protection device according to the second aspect of the invention is designed to minimize the deviations in luminance transmitted between each active zone of the adaptive screen.

By way of a non-limiting example, an individual is considered, wearing such a protective device and looking at a view with a strong luminous contrast, comprised of a dark region and a bright region. A first active zone of the adaptive screen, aligned firstly with the eyes of the individual and secondly with the dark region, can be configured such that its transmittance is equal or close to the maximum value—typically equal to 1—in order to be transparent and permit the passage of the majority of incident light rays on said first active zone. Conversely, a second active zone of the adaptive screen, aligned firstly with the eyes of the individual and secondly with the bright region, can be configured such that its transmittance is equal or close to the minimum value—typically equal to 0—in order to be more opaque than the first active zone and to attenuate, to a substantial extent, the incident light rays on said second active zone.

The active zones of the adaptive screen of such an optical protection device can constitute a variety of geometric zones, according to the considerations applied. By way of non-limiting examples, the active zones of such an adaptive screen can be arranged adjacently, two-by-two, wherein each active zone extends from one edge of the adaptive screen to the other. According to a first form of embodiment, the active zones can be configured in horizontal strips, wherein the active zones are arranged adjacently, two-by-two, in the vertical direction, wherein each active zone is separated from the adjacent active zone by an inactive zone. According to a second form of embodiment, the active zones can be configured in vertical strips, wherein the active zones are arranged adjacently, two-by-two, in the horizontal direction, wherein each active zone is separated from the adjacent active zone by an inactive zone. According to further forms of embodiment, the active zones can extend in any direction, according to the applications considered. Where applicable, the active zones can be matched with certain specific ophthalmological zones in a pair of spectacles or a motorbike helmet visor, in order to correspond, for example, to a first zone which is adapted to close-up vision, and a second zone which is adapted to long-distance vision. Further configurations will be described hereinafter, by way of examples.

Specifically, examples and technical characteristics relating to the active zones of the adaptive screens described according to the first, third and fourth aspects of the invention apply, mutatis mutandis, to the adaptive screen of the optical protection device.

The optical protection device according to the second aspect of the invention can advantageously comprise at least one of the following refinements, wherein the constituent technical characteristics of said refinements can be considered individually or in combination:

the optical protection device is of the motorbike helmet type, wherein the support forms at least part of a shell of said motorbike helmet, and a visor of said motorbike helmet is formed by at least one part of the adaptive screen. Naturally, according to the dimensions of the adaptive screen, the response times of the different active zones can vary. In general, however, the adaptive screen according to the first aspect of the invention permits the reduction of the response time of at least one active zone in relation to an adaptive screen of identical size comprising only a single active zone;

the optical protection device is of the pair of spectacles type, wherein the support forms a frame of said pair of spectacles, and at least part of a lens of the pair of spectacles is formed by the adaptive screen;

the optical protection device incorporates an electrical energy storage device, which is electrically connected to at least one electrical conductor, for the electrical polarization of the at least one shutter in at least one active zone. Preferably, the energy storage device is accommodated in the support of the optical protection device, for example in the frame of the pair of spectacles, or in the shell of the helmet. The energy storage device can assume the form of any known electrical battery;

the at least one shutter comprises a plurality of liquid crystals and at least one polarizer, which permits the configuration of the corresponding shutter between the passing configuration and the blocked configuration;

the at least one shutter comprises a liquid crystal mixture and at least one polarizer, which permits the configuration of the corresponding shutter between the passing configuration and the blocked configuration;

the at least one shutter comprises a liquid crystal mixture with at least one dichroic and/or chiral dopant, which can be configured between the passing configuration and the blocked configuration;

the at least one shutter comprises a plurality of liquid crystals with at least one dichroic and/or chiral dopant, which can be configured between the passing configuration and the blocked configuration. The dichroic and/or chiral dopant shows properties of absorption and/or reflection, where it is used in combination with liquid crystals, and specifically where the concentration of dichroic and/or chiral dopant is sufficient. In this particular form of embodiment of the invention, the dopants present can be oriented in the direction of the liquid crystal molecule directors;

the optical protection device incorporates an electrical energy storage device, which is electrically connected to at least one of the electrical conductors, for the modification of the configuration of dichroic dopant in at least one active zone;

the optical protection device comprises a control unit which is configured to generate the control signal for the switchover of the at least one shutter in at least one active zone between the passing configuration and the blocked configuration. The control unit is electrically connected to said active zones by means of electrical connecting wires. Preferably, the control unit is accommodated in the support of the optical protection device, for example in the frame of the pair of spectacles, or in the shell of the helmet;

the control unit generates at least one control signal per active zone, in order to configure a predetermined average transmittance of each active zone;

the optical protection device further comprises a photodetector, which is designed to measure at least one luminous intensity, wherein the at least one control signal is defined as a function of the luminous intensity thus measured. The photodetector can assume, for example, the form of a camera, for example of the CMOS type (Complementary Metal-Oxide Semiconductor) or CCD type (Charge Coupled Device). Preferably, the photodetector is accommodated in the support of the optical protection device, for example in the frame of the pair of spectacles, or in the shell of the helmet. Preferably, it is situated in proximity to the adaptive screen, between the individual wearing the optical protection device and the adaptive screen or, alternatively, on the opposing side of the adaptive screen, in relation to said individual.

According to a third aspect of the invention, a driver assistance system for a motor vehicle is proposed, comprising:

an adaptive screen according to the first aspect of the invention, or one of the refinements thereof;

a control unit for at least one part of the active zones of the adaptive screen, wherein the control unit is configured to generate at least one control signal for the at least one shutter of the adaptive screen.

The invention, according to its third aspect, thus permits the improvement of the visual comfort of a driver of a motor vehicle, specifically with regard to the brightness perceived by said driver. More specifically, the control unit permits the configuration of each active zone of the adaptive screen as a function of at least the brightness of a view of the road situated to the front of the motor vehicle and perceived by the driver through said adaptive screen.

In general, the term motor vehicle is considered here in its broadest sense, as a—specifically motorized—wheeled vehicle. By way of non-limiting examples, this may include a car, a motorbike, a truck or a bus.

The control unit can assume the form of a microcontroller or a microprocessor.

In a comparable manner to the first and second aspects of the invention, the invention, according to its third aspect, advantageously permits the configuration of the transmittance of each active zone as a function of the part of the view of the road which is situated in the axis of each corresponding active zone, in relation to the eyes of the driver. The transmittance of each active zone is thus configured in order to obtain the compliance of a given luminance transmitted with a predefined value, in the interests of improving the visual comfort of the driver.

The control unit of such a driver assistance system can, for example, be configured such that the luminance transmitted is uniform, or substantially uniform, over all or part of the surface area of the adaptive screen, i.e. over all or part of the active zones. At the very least, the driver assistance system according to the third aspect of the invention is designed to minimize the deviations in luminance transmitted between each active zone of the adaptive screen.

By way of a non-limiting example, a driver is considered who is wearing such a protective device and looking at a view of the road in direct sunlight. This type of view of the road can feature strong luminous contrasts, wherein the part of the view situated above the horizon can be very bright, particularly if the sun is directly visible, whereas the median region, corresponding to the part of the road situated to the front of the motor vehicle, can show a substantially lower brightness, in comparison with the upper region. Thus, a first active zone of the adaptive screen aligned firstly with the eyes of the driver and secondly with the part of the view of the road corresponding with the road to the front of the motor vehicle, can be configured by the control unit such that its transmittance is equal or close to the maximum value—typically equal to 1—in order to be transparent and permit the passage of the majority of the incident luminous flux on said first active zone. Conversely, a second active zone of the adaptive screen, aligned firstly with the eyes of the driver and secondly with the part of the view of the road situated above the horizon, can be configured by the control unit such that its transmittance is equal or close to the minimum value—typically equal to 0—in order to be more opaque than the first active zone and to attenuate the incident luminous flux on said second active zone.

The active zones of the adaptive screen in such a driver assistance system can constitute a variety of geometric zones, according to the considerations applied. By way of non-limiting examples, the active zones of such an adaptive screen can be arranged adjacently, two-by-two, wherein each active zone extends from one edge of the adaptive screen to the other. According to a first form of embodiment, the active zones can be configured in horizontal strips, wherein the active zones are arranged adjacently, two-by-two, in the vertical direction, wherein each active zone is separated from the adjacent active zone by an inactive zone. According to a second form of embodiment, the active zones can be configured in vertical strips, wherein the active zones are arranged adjacently, two-by-two, in the horizontal direction, wherein each active zone is separated from the adjacent active zone by an inactive zone. According to further forms of embodiment, the active zones can extend in any direction, according to the applications considered. Where applicable, the active zones can be matched with certain specific ophthalmological zones in a pair of spectacles or a motorbike helmet visor, in order to correspond, for example, to a first zone which is adapted to close-up vision, and a second zone which is adapted to long-distance vision. Further configurations will be described hereinafter, by way of examples.

The driver assistance system according to the third aspect of the invention can advantageously comprise at least one of the refinements described below, wherein the technical characteristics constituting said refinements can be considered individually or in combination:

- the control unit is configured to switch over the at least one shutter in the corresponding active zone between the passing configuration and the blocked configuration, wherein each active zone is controlled by a control signal which is the same as, or different from the control signal of other active zones. In this manner, each active zone of the adaptive screen is controlled independently of the other active zones, in order to adjust its transmittance as a function of the part of the view of the road with which it is associated, i.e. preferably the part of the view of the road which is substantially aligned with—or adjacently to—the eye of the driver of the motor vehicle. To this end, at least one control parameter for the control signal associated with at least one active zone is different from the control parameter associated with another active zone. By way of non-limiting example, a first active zone can be configured with a first duty cycle, a second active zone can be configured with a second duty cycle which differs from the first duty cycle, and a third active zone can be configured by means of a control signal having a switching frequency which differs from that of the first and second active zones;
- the driver assistance system further comprises (i) a photodetector which is designed to detect at least one ray of light which strikes the motor vehicle from a view of the road situated to the front of said motor vehicle; and (ii) a processing unit which is configured to determine a luminous intensity of the ray of light, wherein the at least one control signal generated by the control unit is determined as a function of luminous intensity. A driver assistance system of this type thus permits the configuration of each active zone as a function of the ray of light which strikes the motor vehicle, and the measurement of the associated luminous intensity. Thereafter, by the comparison, for example of the luminous intensity of the ray of light striking the motor vehicle with a threshold value which corresponds to a value of luminous intensity which is comfortable for the driver, the processing unit transmits a parameter to the control unit which permits the determination of the extent to which the luminous flux of light rays striking the motor vehicle is to be absorbed by the adaptive screen, such that only a proportion of the light rays striking the motor vehicle are transmitted to the driver. Naturally, this processing function is executed for each active zone, in an independent manner. Each active zone can be associated with a particular threshold value. The threshold values can also change over time, as a function of the use and the location of the motor vehicle. For example, first threshold values can be defined for daytime use of the motor vehicle, and second threshold values can be defined for night-time use;
- the photodetector is situated between the adaptive screen and a driver of the motor vehicle, wherein the ray of light firstly passes through the adaptive screen before striking said photodetector. This judicious configuration permits the improvement of accuracy of measurements executed, and the improvement of the comfort achieved using such a driver assistance system. In this case, the photodetector is designed to measure a luminous intensity, as perceived by the eye; the correction executed in combination by the processing unit and the control unit for the configuration of active zones on the screen in order to attenuate a proportion of the luminous intensity which reaches the adaptive screen is thus more accurate than in a case where the photodetector is situated in a more remote configuration in relation to the eye, and specifically on the other side of the adaptive screen in relation to the eye;
- at least one active zone of the adaptive screen is configured to reduce dazzle and/or glare in the motor vehicle detected by the photodetector, specifically by reducing the luminous intensity of a proportion of the light rays passing through the adaptive screen;
- the adaptive screen is formed by at least part of the windscreen of the motor vehicle, or a screen which is arranged between the windscreen and a driver of the motor vehicle, or by at least one lens of a pair of spectacles worn by the driver of the motor vehicle, or at least part of a visor of a helmet worn by the driver of the motor vehicle;
- where the adaptive screen is formed by the pair of spectacles or the helmet, the adaptive screen comprises at least one active zone, described as the sun-shield zone, situated on an upper part of the adaptive screen and extending laterally from one edge of the adaptive screen to the other. Typically, the sun-shield zone covers a part of the view of the road situated above the horizon. The sun-shield zone is formed by a substantially horizontal band which covers the upper part of the adaptive screen. Where applicable, the sun-shield zone is slightly curved, in accordance with the shape of the adaptive screen, wherein the sun-shield zone principally forms a band of constant width from one lateral edge of the adaptive screen to the other;
- where the adaptive screen is formed by the pair of spectacles or the helmet, the adaptive zone comprises an active zone, described as the close-up vision zone, in a lower corner of the adaptive screen, wherein the surface area of said close-up vision zone is equal to or greater than one quarter of the surface area of the adaptive screen. Typically, the close-up vision zone covers part of the visual field which corresponds to part of the dashboard of the motor vehicle. The close-up vision zone is typically constituted by a surface area which forms a sector of a disc situated on the lower central part of the adaptive screen. More specifically, in the case of a pair of spectacles, the close-up vision zone is constituted by a sector of a disc situated in the lower central corner of each spectacle lens, wherein the sector substantially covers a surface area of one quarter-circle. In the case of a motorbike helmet visor, the close-up vision zone is constituted by a sector of disc situated laterally to the centre, and vertically towards the bottom of said visor, wherein the sector substantially covers a surface area of one half-circle. Where applicable, the close-up vision zone can cover a band which extends laterally from one edge of the adaptive screen to the other, and is of constant width;
- the at least one shutter of the close-up vision zone is configured in phase opposition to the interior lighting of the motor vehicle, in order to permit the attenuation of the contrast in luminous intensity between the beams emitted by a lighting device of the motor vehicle and the interior lighting of said motor vehicle. This characteristic is particularly advantageous for night-time driving, as a means of improving the comfort and reducing the visual fatigue of the driver;

where the adaptive screen is formed by the pair of spectacles or the helmet, the adaptive screen comprises an active zone, described as the driving zone, situated in a central zone of the adaptive screen and extending laterally from one edge of the adaptive screen to the other, wherein the surface area of said driving zone is equal to or greater than one half of the surface area of the adaptive screen. Typically, the driving zone covers part of the visual field corresponding to the view of the road situated to the front of the motor vehicle, and specifically the road itself. The driving zone is typically constituted by a curved surface area, extending laterally from one edge of the adaptive screen to the other and situated, for example, between the close-up vision zone and the sun-shield zone. The driving zone can be narrower in a central zone of the adaptive screen, and broader at the edges of the adaptive screen. Alternatively, the driving zone can assume the form of a band of constant thickness, extending laterally from one edge of the adaptive screen to the other;

the driving zone is designed to cover a zone perceived by the driver which encompasses at least part of the view of the road;

the driver assistance system comprises an oculometer, which is designed to measure a movement of the eyes of the driver of the motor vehicle and/or a device for tracking a movement of the head of the driver of the motor vehicle, wherein at least one active zone of the adaptive screen is configured as a function of said movement of the eyes and/or of said movement of the head respectively.

According to a fourth aspect of the invention, a motor vehicle is proposed comprising (i) at least one lighting device which is designed to emit a beam for the illumination of the road situated to the front of the motor vehicle, (ii) a driver assistance system according to the second aspect of the invention, or according to any of the refinements thereof, wherein said driver assistance system is designed to determine the at least one parameter for the control signal of the adaptive screen, and to control the illumination of at least one light source of the lighting device, as a function of said at least one parameter.

The motor vehicle according to the fourth aspect of the invention can advantageously comprise at least one of the refinements described below, wherein the technical characteristics constituting said refinements can be considered individually or in combination:

the at least one shutter of at least one active zone of the adaptive screen is synchronized with the at least one light source of the lighting device. More specifically, the switching frequency and/or switching phase of the control signal of the at least one shutter of at least one active zone of the adaptive screen is synchronized with the at least one light source. In other words, a control unit which controls the emission of the light beam emitted by the light sources of the lighting device is configured to transmit a synchronization signal to the control unit of the driver assistance system, in order to synchronize at least one active zone, for example by adjusting the switching frequency of the control signal of at least one active zone to the same frequency as a pulse frequency of the lighting device. This advantageous characteristic specifically permits the adjustment of a brightness contrast between at least one active zone and the lighting device of said motor vehicle;

the at least one shutter of at least one active zone of the adaptive screen switches in phase with the at least one light source of the lighting device.

Varying forms of embodiment of the invention are provided, incorporating the various optional characteristics described herein, in accordance with all the potential combinations thereof.

DESCRIPTION OF THE FIGURES

Further characteristics and advantages of the invention proceed firstly from the following description, and secondly from a number of exemplary embodiments, which are provided by way of indication and not by way of limitation, with reference to the schematic drawings attached hereto, wherein:

FIGS. 1a and 1b illustrate two shutters of an adaptive screen according to the first aspect of the invention;

FIGS. 2a and 2b illustrate two variants of embodiment of an optical protection device, assuming the form of a pair of spectacles according to the second aspect of the invention;

FIGS. 3a and 3b illustrate two variants of embodiment of an optical protection device, assuming the form of a motorbike helmet according to the second aspect of the invention;

FIG. 4 illustrates a schematic view of a driver assistance system, according to the third aspect of the invention.

Naturally, the characteristics, variants and different forms of embodiment of the invention can be mutually associated, in various combinations, provided that they are not incompatible or mutually exclusive. Specifically, variants of the invention are conceivable which comprise only a selection of the characteristics described hereinafter, in isolation from the other characteristics described, if this selection of characteristics is sufficient to confer a technical advantage, or to differentiate the invention in relation to the prior art.

Specifically, all the variants and all the forms of embodiment described are mutually combinable, and there is no technical obstacle to this combination.

In the figures, elements which are common to a number of figures are identified by the same reference symbols.

DETAILED DESCRIPTION OF THE INVENTION

With reference to FIGS. 1a and 1b, a shutter is described of the type deployed in an adaptive screen according to the first aspect of the invention.

FIG. 1a represents a shutter 400 of an adaptive screen in its simplest form, wherein said shutter constitutes an active zone of the adaptive screen. A shutter 400 of this type comprises a liquid crystal cell 410 arranged between two transparent substrates 420. Each substrate comprises an electrode 430 which permits the application of a non-zero electric field to the interior of the liquid crystal cell 410 in order to execute the switchover of the shutter 400 between the passing configuration and the blocking configuration, as described above.

FIG. 1b represents a shutter 400 of an adaptive screen, wherein said shutter 400 forms two adjacent active zones for the adaptive screen. A shutter 400 of this type comprises a liquid crystal cell 410 arranged between two transparent substrates 420. The upper substrate 420 comprises two adjacent electrodes 430 arranged with a mutual spacing, and the lower substrate 420 comprises one electrode 430 situated in an intermediate position between the two electrodes 430 of the upper substrate. The three electrodes 430 collectively permit the application of a non-zero electric field to the interior of the liquid crystal cell 410, for each of the active zones, thereby permitting the switchover of the shutter 400 between the passing configuration or the blocking configuration, as described above.

With reference to FIGS. 2a and 2b, a pair of spectacles 150, constituting an optical protection device 10, comprises a first lens 151 and a second lens 152, which are interconnected by a frame 153.

Each lens 151, 152 in the pair of spectacles 150 comprises an adaptive screen 100. Each adaptive screen advantageously extends over the full surface area of each corresponding lens 151, 152.

Each adaptive screen 100 comprises a plurality of active zones and, more specifically, three active zones:
  a first active zone 121 is situated on an upper part of a lens 151, 152;
  a second active zone 122 is situated on an intermediate part of a lens 151, 152;
  a third active zone 123 is situated on a lower zone of a lens 151, 152.

Each active zone 121-123 comprises at least one shutter, as described above, preferably of the liquid crystal type.

Specifically, the at least one shutter of each active zone 121-123 is designed to be activated between the passing configuration and the blocking configuration by means of an electric field applied between two electrodes which flank said at least one shutter.

According to a first form of embodiment, the at least one shutter assumes the form of liquid crystals associated with at least one optical polarizer, wherein the activation of said at least one shutter thus assumes the form of optical polarization.

According to a second form of embodiment, the at least one shutter comprises liquid crystals and at least one dichroic and/or chiral dopant, wherein the activation of said shutter thus assumes the form of optical absorption or reflection.

For the electrical polarization of the at least one shutter of each active zone 121-123, each active zone 121-123 comprises at least one electrical connection interface 131-133 which permits the electrical connection of electrically-conductive wires for the routing of a control signal from a control unit, which is not represented, to the electrodes.

The electrical connection interfaces 131-133 are advantageously situated at the periphery of at least one part of each corresponding active zone 121-123, and further preferably at the periphery of each adaptive screen 100.

More specifically, in the exemplary embodiment illustrated in FIG. 2a:
  the first active zone 121 comprises a single electrical connection interface 131 situated on one part of the upper edge of said first active zone 121. The second active zone 122 comprises two electrical connection interfaces 132 situated on opposing lateral edges of said second active zone 122. The third active zone 123 comprises a single electrical connection interface 133 situated on a lower edge of said third active zone 123;
  the first active zone 121 assumes the form of a band of constant width situated on the upper part of the adaptive screen 100 and the spectacle lens 151, 152, thus forming a surface area which is perceived by the wearer of said pair of spectacles 150 to cover the sky, when they look straight ahead of them. In other words, the first active zone 121 covers a surface which corresponds to the part of the visual field of a driver situated substantially above the horizon, when the driver looks at the road ahead. The first active zone 121 corresponds to the sun-shield zone described above. The first active zone 121 occupies a surface area ranging from 10% to 30% of the total surface area of the adaptive screen 100;
  the third active zone 123 corresponds to the close-up vision zone described above. In general, it is formed by the zones of each lens 151, 152 situated laterally to the side of the frame 153, in a lower zone of the adaptive screen 100. For a driver of a motor vehicle wearing such a pair of spectacles 150, the third active zone 123 corresponds to a surface which covers the part of the visual field of the driver which is substantially situated at the level of the dashboard of said motor vehicle;
  the second active zone 122 corresponds to the principal active zone described above. In general, it is situated in an intermediate position between the first zone 121 and the third zone 123. It covers a surface area which is at least greater than one half of the adaptive screen 100, and preferably ranges between 50% and 60% of the total surface area of the adaptive screen 100. For a driver of a motor vehicle wearing such a pair of spectacles 150, the second active zone 122 corresponds to a surface area which covers the part of the visual field of the driver which is substantially situated at the level of the view of the road to the front of said motor vehicle, specifically the road on which the motor vehicle is located.

Each active zone 121-123 is separated from the directly adjacent active zone by an inactive zone 110 of width equal to or less than 2 µm, such that it is not perceptible by the wearer of the pair of spectacles 150. The inactive zone, where applicable, can comprise at least one shutter which is not addressed by the electrodes and/or the electrical connection interfaces, or may not incorporate such shutters.

The electrical connecting wires are preferably integrated in the frame 153 of the pair of spectacles 150.

FIG. 2b illustrates a further variant of embodiment of the pair of spectacles 150 described above, in which the active zones 121-123 of each adaptive screen 100 are defined and delimited more simply. More specifically:
  the electrical connection interface 135 is situated over the entire peripheral outline of each spectacle lens 151, 152, such that each active zone is addressed by part of the electrical interface 135. More specifically, each peripheral element situated at the edge of the spectacle lens 151, 152 in each active zone 121-123 comprises a connection interface 135 which permits the activation of the corresponding active zone. Each electrical interface 135 of each active zone is electrically connected to at least one electrical connecting wire, in order to permit the routing of a control signal;
  the first active zone 121 assumes the form of a band situated on the upper part of the adaptive screen 100 and the spectacle lens 151, 152 and separated from the second active zone 122 by a straight and preferably horizontal inactive zone 110. The first active zone 121 occupies a surface area ranging from 10% to 30% of the total surface area of the adaptive screen 100;
  the third active zone 123 assumes the form of a band situated on the lower part of the adaptive screen 100 and the spectacle lens 151, 152 and separated from the second active zone 122 by a straight and preferably horizontal inactive zone 110. The third active zone 123 occupies a surface area ranging from 10% to 30% of the total surface area of the adaptive screen 100;

the second active zone 122 is situated in an intermediate position between the first active zone 121 and the third active zone 123. It occupies a surface area which is at least greater than one half of the adaptive screen 100, and preferably ranges between 50% and 60% of the total surface area of the adaptive screen 100. It is separated from the third active zone 123 and from the first active zone 121 by a straight and preferably horizontal inactive zone 110.

Each active zone 121-123 is separated from the directly adjacent active zone 121-123 by an inactive zone 110 of width equal to or less than 2 μm, such that it is not perceptible by the wearer of the pair of spectacles 150. The inactive zone, where applicable, can comprise at least one shutter which is not addressed by the electrodes and/or the electrical connection interfaces, or may not incorporate such shutters.

The electrical connecting wires are preferably integrated in the frame 153 of the pair of spectacles 150.

FIGS. 3a and 3b illustrate a motorbike helmet 250 constituting an optical protection device 20, comprising a visor 251 which is integrated in a shell 253 in a moveable manner.

The visor 251 comprises an adaptive screen 200 which advantageously extends over the full surface area of the visor 251. The adaptive screen 200 comprises a plurality of active zones 221-223 and, more specifically, three active zones:
  a first active zone 221 is situated on an upper part of the visor 251;
  a second active zone 222 is situated on an intermediate part of the visor 251;
  a third active zone 223 is situated on a lower zone of the visor 251.

Each active zone 221-223 comprises at least one shutter, as described above, preferably of the liquid crystal type.

Specifically, the at least one shutter of each active zone 221-223 is designed to be activated between the passing configuration and the blocking configuration by means of an electric field applied between two electrodes which flank said shutters.

According to a first form of embodiment, the at least one shutter assumes the form of liquid crystals associated with at least one optical polarizer, wherein the activation of said at least one shutter assumes the form of optical polarization.

According to a second form of embodiment, the at least one shutter comprises liquid crystals and at least one dichroic and/or chiral dopant, wherein the activation of said shutter thus assumes the form of optical absorption and/or reflection.

For the electrical polarization of the at least one shutter of each active zone 221-223, each active zone 221-223 comprises at least one electrical connection interface 231-233 which permits the electrical connection of electrically-conductive wires for the routing of a control signal from a control unit, which is not represented, to the electrodes.

The electrical connection interfaces 231-233 are advantageously arranged at the periphery of at least one part of each corresponding active zone 221-223, and further preferably at the periphery of each adaptive screen 200.

More specifically, in the exemplary embodiment illustrated in FIG. 3a:
  the first active zone 221 comprises two electrical connection interfaces 231, situated on one part of each lateral edge of said first active zone 221. The second active zone 222 comprises two electrical connection interfaces 232 situated on opposing lateral edges of said second active zone 222. The third active zone 223 comprises a single electrical connection interface 233 situated on a lower edge of said third active zone 223;
  the first active zone 221 assumes the form of a band of constant width situated on the upper part of the adaptive screen 200 and the visor 251, thus forming a surface which is perceived by the wearer of said motorbike helmet 250 to cover the sky, when they look straight ahead of them. In other words, the first active zone 221 covers a surface area which corresponds to the part of the visual field of a motorbike driver situated substantially above the horizon, when the latter looks at the road ahead. The first active zone 221 corresponds to the sun-shield zone described above. The first active zone 221 occupies a surface area ranging from 10% to 30% of the total surface area of the adaptive screen 200;
  the third active zone 223 corresponds to the close-up vision zone described above. In general, it is constituted with an essentially semi-circular disc shape, the base of which is formed by the lower edge of the visor 251. For a driver of a motorbike wearing such a motorbike helmet 250, the third active zone 223 corresponds to a surface area which covers the part of the visual field of the driver which is substantially situated at the level of the dashboard of said motorbike;
  the second active zone 222 corresponds to the principal active zone described above. In general, it is situated in an intermediate position between the first zone 221 and the third zone 223. It covers a surface area which is at least greater than one half of the adaptive screen 200, and preferably ranges between 50% and 60% of the total surface area of the adaptive screen 200. For a driver of a motorbike wearing such a motorbike helmet 250, the second active zone 222 corresponds to a surface area which covers the part of the visual field of the motorbike driver which is substantially situated at the level of the view of the road to the front of said motorbike, specifically comprising the road on which the motorbike is located.

Each active zone 221-223 is separated from the directly adjacent active zone by an inactive zone 210 of width equal to or less than 2 μm, such that it is not perceptible by the wearer of the motorbike helmet 250. The inactive zone 210, where applicable, can comprise shutters which are not addressed by the electrodes and/or the electrical connection interfaces, or may not incorporate such shutters.

The electrical connecting wires are preferably integrated in the motorbike helmet 250, preferably at the level of the shell 253.

FIG. 3b illustrates a further variant of embodiment of the motorbike helmet 250 described above, in which the active zones 221-223 of the adaptive screen 200 constituting the visor 251 are defined and delimited more simply. More specifically:
  the electrical connection interface 235 is situated over the entire peripheral outline of the visor 251, such that each active zone 221-223 is addressed by part of the electrical interface 235. More specifically, each peripheral element situated on the edge of the visor 251 in each active zone 221-223 comprises an electrical connection interface 235 which permits the polarization of the corresponding active zone. Each electrical connection interface 235 of each active zone 221-223 is electrically connected to at least one electrical connecting wire, in order to permit the routing of a control signal;
  the first active zone 221 assumes the form of a band situated on the upper part of the adaptive screen 200 and of the visor 251. The first active zone 221 is separated from the second active zone 222 by a straight and preferably horizontal inactive zone 210. The first active zone 221 occupies a surface area ranging from 10% to 30% of the total surface area of the adaptive screen 200;

the third active zone 223 assumes the form of a band situated on the lower part of the adaptive screen 200 of the visor 251. The third active zone 223 is separated from the second active zone 222 by a straight and preferably horizontal inactive zone 210. The third active zone 223 occupies a surface area ranging from 10% to 30% of the total surface area of the adaptive screen 200;

the second active zone 222 is situated in an intermediate position between the first active zone 221 and the third active zone 223. It occupies a surface area which is at least greater than one half of the adaptive screen 200, and preferably ranges between 50% and 60% of the total surface area of the adaptive screen 200. It is separated from the third active zone 223 and the first active zone 221 by a straight and preferably horizontal inactive zone 210.

Each active zone 221-223 is separated from the directly adjacent active zone 221-223 by an inactive zone 210 of width equal to or less than 2 µm, such that it is not perceptible by the wearer of the motorbike helmet 250. The inactive zone 210, where applicable, can comprise shutters which are not addressed by the electrodes and/or the electrical connection interfaces, or may not incorporate such shutters.

The electrical connecting wires are preferably integrated in the shell 253 of the motorbike helmet 250.

FIG. 4 illustrates a schematic partial sectional view of a driver assistance system 30 according to the third aspect of the invention.

A motor vehicle 300 is equipped, in a conventional manner, with a lighting device 350 which is designed to emit a light beam onto a view of the road SR, by means of at least one light source. The vehicle 300 is controlled by a driver, who is symbolized by their eye 3. The view of the road SR corresponds to the scene observed by the driver 3 of the vehicle 300. Schematically, the driver 3 observes the view of the road SR to the front of the vehicle 300, and through the windscreen 310.

An adaptive screen is arranged in the field of vision of the driver 3, between the latter and the view of the road SR. According to different forms of embodiment of the invention, the adaptive screen may be comprised of the following:
  a screen 320, preferably arranged between the driver 3 and the windscreen 310. Advantageously, the screen 320 is of foldaway design, in the manner of a sunshield, or of roll-up design;
  the windscreen 310 itself; or
  a pair of spectacles 150 worn by the driver 3, in the manner of sunglasses or corrective spectacles.

For convenience, these three forms of embodiment are represented simultaneously in FIG. 4. However, these are only variants of embodiment, wherein each of these is intended to achieve the same result.

In the remainder of the description, the term "adaptive screen" will be employed indiscriminately to designate one of these three forms of embodiment.

For each of these forms of embodiment, the adaptive screen comprises a plurality of active zones, wherein each active zone is constituted by at least one shutter which is designed to shut-off the corresponding active zone at at least one given oscillation frequency, as described above. Each active zone of the adaptive screen can assume two configurations, consecutively and alternately:
  a first configuration, described as passing, wherein the shutters are designed to permit the passage of a ray of light through said active zone of the adaptive screen;
  a second configuration, described as blocking, wherein the shutters are designed to obstruct the passage of a ray of light through said active zone of the adaptive screen.

According to a first form of embodiment, the at least one shutter assumes the form of liquid crystals associated with at least one optical polarizer, wherein the activation of said at least one shutter thus assumes the form of optical polarization.

According to a second form of embodiment, the at least one shutter comprises liquid crystals and at least one dichroic and/or chiral dopant, wherein the activation of said shutter or shutters thus assumes the form of optical absorption and/or reflection.

Advantageously, each active zone of the adaptive screen is controlled by a control signal which initiates the switchover of the corresponding shutters between the first and second configuration. The control signal is characterized by at least three parameters, which permit the configuration of an average transmittance of the corresponding active zone:
  a switching frequency; and/or
  a switching phase; and/or
  a switching duty cycle, which is advantageously invariable, for example with a value of 50%.

According to the third aspect of the invention, the parameters of each control signal for the control of an active zone can be controlled and modified as a function of at least one measurement executed on the view of the road by a photodetector 360.

The photodetector 360 is advantageously situated between the adaptive screen and the driver 3. If the adaptive screen is situated on the windscreen 310, the photodetector 360 is then situated to the rear of said windscreen 310, on the interior of the vehicle 30. If the adaptive screen is situated on the screen 320, the photodetector 360 is then situated to the rear of said screen 320, between the screen 320 and the driver 3. If the adaptive screen is situated on the pair of spectacles 150, the photodetector 360 is then situated to the rear of said pair of spectacles 150, between the pair of spectacles 150 and the driver 3. Where applicable, the photodetector 360 can also be situated in front of the pair of spectacles 150.

The photodetector 360 is designed to measure at least one "incident" signal originating from a light source situated in the view of the road, on the other side of the screen from the driver 3. By way of non-limiting example, the photodetector 360 can advantageously comprise a video camera or a photodiode. Preferably, the photodetector is designed for the detection of at least one light ray, the frequency of which falls within the visible spectrum.

The driver assistance system advantageously comprises a control unit 330, which is designed to control each active zone of the adaptive screen. The control unit 330 can advantageously assume the form of a control centre for the vehicle 30.

Preferably, the control unit 330 is connected to another control unit 340 which controls the power supply to the lighting device 350 of the vehicle 30. The lighting device 350 comprises at least one light source which is designed to emit a light beam onto the view of the road SR. Preferably, the light beam is of periodically variable intensity between a maximum value and a minimum value. In other words, the lighting device 350 is configured to emit a pulsed light beam, the luminous intensity and/or pulse frequency and/or pulse phase of which are controlled by a control signal which is generated by said other control unit 340 of the lighting device 350.

Advantageously, the control unit 340 of the lighting device 350 is designed and configured to communicate with the control unit 330 of the driver assistance system, in order to transmit at least one control signal parameter for the control of the lighting device 350.

Where the adaptive screen is, for example, mobile or remote from the control unit 330, specifically in the case of the use of the pair of spectacles 150 or the screen 320, the driver assistance system can comprise a wired or wireless communication device, for example employing a specified wireless communication protocol in accordance, for example, with IEEE standards 802.15.1, and all extensions thereof which are generally known by the registered trademark "Bluetooth" or IEEE 802.11, generally known by the registered trademark "Wifi", and, more specifically, IEEE standard 802.11p concerning the application of wifi in the field of motor vehicles.

Advantageously, the communication device further comprises a wave transmitter-receiver connected to the control unit 330 and at least configured for the transmission to the adaptive screen of at least one control signal, as a function of data measured by the photodetector and/or operating parameters for the lighting device.

In summary, the invention relates to an adaptive screen comprising at least one liquid crystal shutter, wherein at least one of the shutters comprises at least two active zones which are addressed by a control signal which permits the switchover of the at least one corresponding shutter between a passing configuration, in which a transmittance is equal to a maximum value, and a blocking configuration, in which the transmittance is equal to a minimum value, characterized in that a "principal" active zone covers a surface area of the adaptive screen which is equal to or lower than 60% of the surface area of said adaptive screen, in order to reduce the response time of said principal active zone.

The invention also relates to various devices for the deployment of such an adaptive screen including, for example, optical protection devices, a driver assistance system and a vehicle incorporating such a driver assistance system.

Naturally, the invention is not limited to the examples described above, and numerous developments can be applied to these examples without departing from the scope of the invention. Specifically, the various characteristics, forms, variants and forms of embodiment of the invention can be mutually associated in various combinations, insofar as they are not incompatible or mutually exclusive. Specifically, all the variants and forms of embodiment described above are mutually combinable.

The invention claimed is:

1. An adaptive screen comprising at least one liquid crystal shutter, wherein the at least one liquid crystal shutter comprises at least two active zones which are addressed by a control signal which permits the switchover of the at least one liquid crystal shutter between a passing configuration, in which a transmittance is equal to a maximum value, and a blocking configuration, in which the transmittance is equal to a minimum value, wherein a principal active zone covers a surface area of the adaptive screen which is equal to or lower than 60% of the surface area of the adaptive screen, in order to reduce the response time of the principal active zone, wherein the switching frequency of the at least one liquid crystal shutter of the principal active zone is equal to or greater than 200 Hz, wherein the adaptive screen comprises electrical conductors which are electrically connected to electrodes via at least one electrical connection interface, wherein each electrical connection interface is in contact with an active zone, and the contact between the electrical connection interface and the active zone extends over the length of the active zone.

2. The adaptive screen according to claim 1, wherein the adaptive screen comprises at least three electrodes a first part of which is situated on a first side of the at least one liquid crystal shutter, and a second part of which is situated on a second side of the at least one liquid crystal shutter, wherein the electrodes permit the application of a non-zero electric field in respect of each other, for the configuration of the at least one liquid crystal shutter of each active zone in the passing or blocking configuration, wherein each active zone can be configured independently of the other active zones.

3. The adaptive screen according to claim 1, wherein the at least one liquid crystal shutter is configured to respond to at least one control signal parameter, wherein the control signal parameter is selected from a group comprising a switching frequency, a switching phase, and a switching duty cycle.

4. The adaptive screen according to claim 1, wherein the active zones are arranged adjacently, two-by-two, wherein each active zone extends from one edge of the adaptive screen to the other.

5. An optical protection device comprising:
   an adaptive screen comprising:
      at least one liquid crystal shutter, wherein the at least one liquid crystal shutter comprises at least two active zones which are addressed by a control signal which permits the switchover of the at least one liquid crystal shutter between a passing configuration, in which a transmittance is equal to a maximum value, and a blocking configuration, in which the transmittance is equal to a minimum value, wherein a principal active zone covers a surface area of the adaptive screen which is equal to or lower than 60% of the surface area of the adaptive screen, in order to reduce the response time of the principal active zone, wherein the switching frequency of the at least one liquid crystal shutter of the principal active zone is equal to or greater than 200 Hz, and
   a support designed to maintain the adaptive screen in front of the eyes of an individual wearing the optical protection device, wherein the principal active zone of the adaptive screen is positioned in a central zone of the adaptive screen and extends laterally from one edge of the adaptive screen to the other, wherein
   the adaptive screen comprises electrical conductors which are electrically connected to electrodes via at least one electrical connection interface, wherein each electrical connection interface is in contact with an active zone, and the contact between the electrical connection interface and the active zone extends over the length of the active zone.

6. The optical protection device according to claim 5, wherein the optical protection device comprises an electrical energy storage device, which is electrically connected to at least one electrical conductor, for the electrical polarization of the at least one liquid crystal shutter in at least one active zone.

7. The optical protection device according to claim 5, wherein the at least one liquid crystal shutter comprises a liquid crystal mixture and at least one polarizer.

8. The optical protection device according to claim 5, wherein the at least one liquid crystal shutter comprises a liquid crystal mixture with at least one dichroic and/or a chiral dopant.

9. The optical protection device according to claim 5, wherein the optical protection device comprises a controller which is configured to generate the control signal for the switchover of the at least one liquid crystal shutter in at least one active zone between the passing configuration and the blocked configuration.

10. The optical protection device according to claim 5, wherein the optical protection device is of a motorbike helmet type, wherein the support forms at least part of a shell of the motorbike helmet, and a visor of the motorbike helmet is formed by at least one part of the adaptive screen.

11. The optical protection device according to claim 5, wherein the optical protection device is of a pair of spectacles type, wherein the support forms a frame of the pair of spectacles, and at least part of a lens of the spectacles is formed by the adaptive screen.

12. A driver assistance system of a motor vehicle comprising:
an adaptive screen comprising:
at least one liquid crystal shutter, wherein the at least one liquid crystal shutter comprises at least two active zones which are addressed by a control signal which permits the switchover of the at least one liquid crystal shutter between a passing configuration, in which a transmittance is equal to a maximum value, and a blocking configuration, in which the transmittance is equal to a minimum value, wherein a principal active zone covers a surface area of the adaptive screen which is equal to or lower than 60% of the surface area of the adaptive screen, in order to reduce the response time of the principal active zone, wherein the switching frequency of the at least one liquid crystal shutter of the principal active zone is equal to or greater than 200 Hz; and
a controller for at least part of the active zones of the adaptive screen, wherein the controller is configured to generate at least one control signal for the at least one liquid crystal shutter of the adaptive screen in order to initiate the switchover of the at least one liquid crystal shutter of the corresponding active zone between the passing configuration and the blocked configuration, wherein each active zone is controlled by a control signal which is identical to or different from the control signal of the other active zones, wherein
the adaptive screen comprises electrical conductors which are electrically connected to electrodes via at least one electrical connection interface, wherein each electrical connection interface is in contact with an active zone, and the contact between the electrical connection interface and the active zone extends over the length of the active zone.

13. The driver assistance system according to claim 12, further comprising:
a photodetector which is designed to detect at least one ray of light which strikes the motor vehicle from a view of the road situated to the front of the motor vehicle; and
a processor which is configured to determine a luminous intensity of the ray of light, wherein the at least one control signal generated by the controller is determined based on the luminous intensity.

14. The driver assistance system according to claim 13, wherein at least one active zone of the adaptive screen is configured to reduce dazzle and/or glare detected by the photodetector.

15. The driver assistance system according to claim 12, wherein the adaptive screen is constituted by:
at least part of the windscreen of the motor vehicle; or
a screen which is arranged between the windscreen and a driver of the motor vehicle; or
at least one lens of spectacles worn by the driver of the motor vehicle; or
at least part of a visor of a helmet worn by the driver of the motor vehicle.

16. The driver assistance system according to claim 12, wherein the adaptive screen is constituted by the spectacles or the helmet, wherein the adaptive screen comprises:
an active sun-shield zone situated on an upper part of the adaptive screen and extending laterally from one edge of the adaptive screen to the other; and/or
an active close-up vision zone situated in a lower corner of the adaptive screen, wherein the surface area of the close-up vision zone is equal to or greater than one quarter of the surface area of the adaptive screen.

17. The driver assistance system according to claim 16, wherein at least one liquid crystal shutter of the close-up vision zone is configured in phase opposition to an interior lighting of the motor vehicle.

18. The driver assistance system according to claim 13, further comprising an oculometer designed to measure a movement of the eyes of the driver of the motor vehicle and/or a device for tracking a movement of the head of the driver of the motor vehicle, wherein at least one active zone of the adaptive screen is configured based on the movement of the eyes and/or the movement of the head, respectively.

* * * * *